(12) United States Patent
Haveri

(10) Patent No.: US 7,726,176 B2
(45) Date of Patent: Jun. 1, 2010

(54) DETECTOR MOUNTING IN PARAMAGNETIC GAS ANALYZERS

(75) Inventor: Heikki Haveri, Huhmari (FI)

(73) Assignee: General Electric Company, Schenectady, NY (US)

( * ) Notice: Subject to any disclaimer, the term of this patent is extended or adjusted under 35 U.S.C. 154(b) by 423 days.

(21) Appl. No.: 11/548,885

(22) Filed: Oct. 12, 2006

(65) Prior Publication Data

US 2007/0084265 A1    Apr. 19, 2007

(30) Foreign Application Priority Data

Oct. 14, 2005    (EP) .................................. 05109558

(51) Int. Cl.
  *G01N 27/74* (2006.01)
(52) U.S. Cl. .................................. 73/25.02
(58) Field of Classification Search .................. 73/25.02
  See application file for complete search history.

(56) References Cited

U.S. PATENT DOCUMENTS

| | | | |
|---|---|---|---|
| 4,403,186 A | 9/1983 | Kotani et al. | |
| 4,464,926 A * | 8/1984 | Albarda et al. | ............... 324/204 |
| 4,633,705 A | 1/1987 | Merilainen et al. | |
| 4,772,848 A | 9/1988 | Hummel et al. | |
| 4,808,921 A * | 2/1989 | Christensen | ................ 324/204 |
| 4,860,574 A | 8/1989 | Maeda et al. | |
| 5,251,264 A | 10/1993 | Tichy et al. | |
| 5,596,147 A | 1/1997 | Wilda et al. | |
| 2007/0227230 A1 * | 10/2007 | Haveri et al. | ............... 73/24.01 |

* cited by examiner

*Primary Examiner*—John Fitzgerald
(74) *Attorney, Agent, or Firm*—Global Patent Operation; Jonathan E. Thomas

(57) ABSTRACT

The invention relates to paramagnetic gas analyzer with a housing, comprising: an electromagnet with an air gap; power source for said electromagnet; a sample gas conduit and a reference gas conduit into said air gap; an exit conduit communicating with said air gap for removing the intermixed gases; pressure detecting microphones connected to said sample gas conduit and to said reference gas conduit for sensing the gas pressures; as well as electronics. The pressure detecting microphones comprise two independent microphonic membranes that are parallel to each other, their pressure surfaces being to the same direction, or to the opposite directions. The electrical outputs of the microphones provide signals that are proportional to gas pressures in the sample gas and reference gas conduits, and that are further processed in the electronics to eliminate effects of mechanical shocks or the like.

11 Claims, 2 Drawing Sheets

DETECTOR MOUNTING IN PARAMAGNETIC GAS ANALYZERS

BACKGROUND OF THE INVENTION

The invention relates to a paramagnetic gas analyzer with a housing, comprising: an electromagnet that has spaced opposing magnetic poles forming an air gap with a magnetic field therebetween; means for supplying an alternating electrical current or a chopped direct electrical current to said electromagnet; a sample gas conduit and a reference gas conduit opening into said air gap, said sample gas being a gas mixture to be analyzed, and said reference gas having a predetermined concentration of a paramagnetic gas; an exit conduit communicating with said air gap for removing the intermixed sample and reference gases from said air gap; pressure detecting microphones connected to said sample gas conduit and to said reference gas conduit for sensing gas pressures in the respective conduits, and giving respective electrical pressure signals; and electronics connected to said microphones to receive said electrical pressure signals to form an analyzer output signal.

Patent publication U.S. Pat. No. 4,633,705 describes a principle and apparatus for a paramagnetic analyzer for measurement of oxygen contents of gas mixtures utilizing the difference between susceptibilities of the sample gas and the reference gas. The analyzer comprises electromagnet in a closed cavity controlled with chopped DC-current, sample and reference gas conduits entering the cavity and magnet core and common exit conduit. Gases are led to the magnetic field in the gap between magnet poles through holes drilled into the magnet core so that pedestals in the gap guide gas flows to collide to be mixed. The mixed gas flows freely out from the gap to the surrounding cavity space. This publication does not specifically define receiving and processing of the measuring signal or measuring signals, but mentions generally that a single microphone could be used, i.e. discloses acoustic detection of the signal. Patent publication U.S. Pat. No. 4,860,574 discloses thermomagnetic type of sensor, magnetic susceptibility type of sensor with diamagnetic dumbbells for detection, and magnetic pressure type detector with e.g. one capacitor microphone for detection as the prior art, whereupon magnetic pressure type detector is mentioned to be sensitive to mechanical vibrations and shocks. As the solution, the publication suggests a pair of thermistors with a large resistance temperature coefficient together with temperature control circuits and a subtracting circuit, instead of acoustic detection with a microphone, to be used for detecting the gas streams.

Patent publication U.S. Pat. No. 4,403,186 discloses a magnetic paramagnetic gas analyzer with acoustic detection. The analyzer includes a measuring chamber for containing a gas to be measured and a comparison gas, wherein the concentration of paramagnetic gas in the gas to be measured is detected from a surface-pressure generated within the measuring chamber between the gas to be measured and the comparison gas, said surface-pressure being due to a difference of magnetizing coefficients of the gas to be measured and the comparison gas passing through magnetic fields generated alternatively between first and second pairs of magnetic pole pieces located within said measuring chamber. Said surface-pressure is detected by a single condenser microphone that has a pair of fixed poles and one condenser film therebetween, the opposite sides of the condenser film communicating with the first and second passageways providing the comparison gas into the two gaps of the two magnetic pole pieces. Accordingly, the detection of surface-pressure is performed on the basis of a differential pressure between the two pairs of magnetic pole pieces when a magnetic field is generated alternatively between the two pairs of magnetic pole pieces. Finally the signals taken out from said fixed poles of said condenser-microphone are amplified by two separate amplifiers respectively, they are added by a differential amplifier and then are introduced into an oxygen content indicating portion.

Patent publication U.S. Pat. No. 4,808,921 also discloses a paramagnetic gas analyzer with acoustic detection. The analyzer comprises an electromagnet with an almost closed ferromagnetic circuit and a gap, including a measuring chamber with inlet and outlet lines for the gas to be analyzed as well as a gas of known magnetic susceptibility. It is provided devices that measure the differential gas pressures in the respective lines by supplying an AC current to the electromagnetic. To reduce the power consumption of the analyzer this patent suggests superimposing a DC magnetic field generated by means of a permanent magnet onto the AC magnetic field attained by an electromagnet, whereupon higher magnetic frequencies, e.g. 100-200 Hz, can be achieved instead of comparatively low frequencies, e.g. 10 Hz, of mechanical systems that are sensitive to noise and vibrations. The amplitude of the measuring result depends on the product of the AC field and the DC field. If the DC field is strong enough, the AC field and thus the supplied power can be reduced accordingly. The latter also facilitates the filtering off of predetermined, undesirable false signals because they have a frequency of $2 \times \omega$, i.e. twice the measuring frequency. The paramagnetic analyzer described can be combined with a photoelectric measuring apparatus including a second measuring chamber and a light source. In either case one pressure signal is measured by means of a first microphone, which is in communication with the feeding line of the anesthetic gas, and another pressure signal is measured by means of a second microphone, which is in communication with feeding line of a reference gas. The electric signals from the microphones are then fed into a differential amplifier, indicating the oxygen concentration. The microphones comprise nickel membranes, but nothing else is described thereof in the publication.

BRIEF DESCRIPTION OF THE INVENTION

It is an object of the invention to attain a gas analyzer for measuring the content of paramagnetic gas component in a gas mixture, which gas analyzer would not be sensitive for mechanical shocks and vibration, i.e. shocks and vibration interfering with the magnetic pressure measurement of the gas should be minimized. Furthermore the analyzer electronics should become simpler and the analyzer size smaller without using additional or complicated electronics.

These objects are achieved by the features defined in claim 1. According to the inventive concept the pressure measuring devices are fixed together and positioned symmetrically in respect to each other so that, besides measuring the magnetic pressure of gas as intended, they sense the mechanical vibration otherwise interfering the measurement as well. This way the mechanical vibration affect both of the magnetic pressure measurement devices similarly, whereupon their electrical outputs correspond to each other. The analyzer output signal is a subtraction or a sum of the electrical output signals from the magnetic pressure measuring devices. The value of e.g. the oxygen content in the measured gas mixture is thus an accurate differential signal whereas the interference caused by the mechanical shock or vibration is automatically eliminated. In the preferred embodiment of the invention it is measured the oxygen content in a respiratory gas mixture, whereupon the measurement is based on the paramagnetic properties of oxygen molecules. In this case oxygen is the only clearly paramagnetic gas, its molecules are attracted by a magnetic field whereas other gases being weakly diamagnetic are repelled by it. Molecules can experience the force only in areas of the magnetic field gradient and therefore, a pressure difference is generated between the gas inside and outside the magnetic field.

The invention is described below in detail with reference to the accompanying drawings, in which

DETAILED DESCRIPTION OF THE INVENTION

Figure 1:
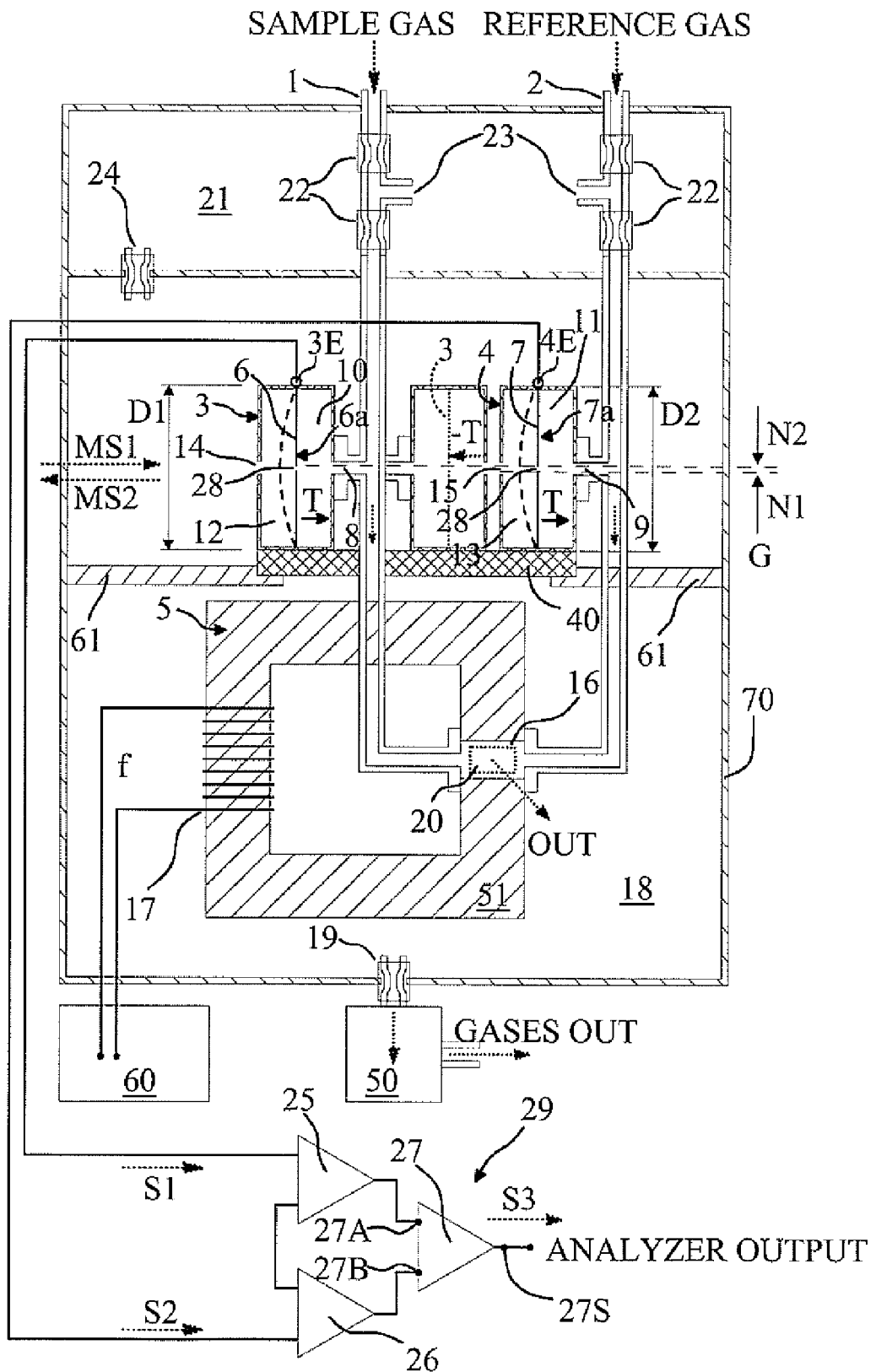
FIG. 1 shows schematically the gas analyzer according to the invention having two detecting microphones, which are positioned in so that the membranes are parallel and to the same direction, or to the opposite directions the other microphone shown in thinner lines and referred to by a dotted line.

The paramagnetic gas analyzer comprises the sample gas conduit 1 and the reference gas conduit 2 as inlets for gases or gas mixtures, which gas conduits extend and open to an air gap 16 of an electromagnet 5. The sample gas is a gas mixture to be analyzed, and the reference gas has a predetermined concentration of a paramagnetic gas or some other gas. The electromagnet 5 has an electric coil 17 and a core 51 of ferromagnetic material that has spaced opposing magnetic poles forming the air gap 16 with a magnetic field therebetween. Hereby a magnetic circuit is formed. The gas analyzer comprises power source 60 for supplying either an alternating electrical current or a chopped direct electrical current to the electric coil 17 of the electromagnet 5, whereupon the magnetic field in the air gap varies respectively. This kind of power source is generally known, and is not explained in detail. Between the conduits 1 and 2 there is connected a pressure equalizer comprising firstly inlet pneumatic suppressors 22, e.g. in the form of chokes for gas flows, balancing openings 23 and a first common volume 21, into which the balancing openings 23 are connected. Typically there are two suppressors in series in both gas conduits and the opening is positioned between these series connected suppressors, as shown in FIG. 1. This pressure equalizer between the conduits 1 and 2 further comprises an exit opening 20 from the air gap 16 to a second common volume 18 for the mixed up reference and sample gases to remove the intermixed gases from the analyzer through an outlet pneumatic suppressor 19, and also a bypass suppressor 24 between the first and the second common volume 21 and 18. The outlet pneumatic suppressor 19 forms a pneumatic filter together with the second common volume 18. The bypass suppressor 24 maintains a small bypass flow from the sample gas conduit 1 and reference gas conduit 2 through openings 23 to volume 18 preventing the gases inside the volume 21 to mix with the sample and the reference gases flowing through gas conduits 1 and 2, whereupon the bypass suppressor 24 forms a pneumatic filter together with the common volumes 21 and 18. This is only one of the possible pressure equalizer arrangements, and it is possible to use other kinds of components and/or other kinds of arrangements, too. The mentioned components or said other kind of components and other possible components are attached to a housing 70, which can be of any known or new type/construction/structure suitable for the purpose, like a case, a cage, a box, or a rack or a combination of one or several of these. Accordingly, the housing 70 of the paramagnetic gas analyzer acts as a support for the components, but it or part of it can be designed and made to form the above-mentioned common volumes 21 and 18. The second common volume 18 and the outlet pneumatic suppressor 19 together can be considered to form the exit conduit for the intermixed sample and reference gases coming out from the air gap 16 of the electromagnet 5.

For attaining gas flows through the gas conduits 1, 2 there is fluctuation means 50, typically a pump arranged at the exit conduit after air gap exit opening 20, i.e. at said second common volume 18, or preferably at the outlet pneumatic suppressor 19, as shown in FIG. 1. It shall be understood that any fluctuation means in any position causing the required gas flow can be utilized. A person skilled in the art can design an appropriate fluctuation mean for the intended use of the paramagnetic gas analyzer, and accordingly it is not described in detail. The paramagnetic gas analyzer further comprises magnetic pressure sensing devices communicating with both gas conduits 1 and 2 through openings or passageways 8 and 9. Preferably these pressure sensing devices are pressure detecting microphones 3 and 4 connected to said sample gas conduit 1 and to said reference gas conduit 2, whereupon they sense gas pressures in the respective conduits, and give respective electrical pressure signals S1, S2. Accordingly, the microphones are for measuring the gas pressures within two conduits. There is also electronics 29 connected to said microphones to receive said electrical pressure signals S1, S2 to form an analyzer output signal S3, as is more in detail explained later in this description.

According to the invention the pressure detecting microphones 3, 4 in the paramagnetic gas analyzer comprise two microphonic membranes 6, 7 that are independent from each other, i.e. one of the microphonic membranes 6 is in the first microphone 3, and another of the microphonic membranes 7 is in the second microphone 4. Especially, the movement of the first membrane 6 caused by the gas pressure in the sample gas conduit 1 is and shall be independent of the movement of the second membrane 7 caused by the gas pressure in the reference gas conduit 2. This does not exclude that alternative that both microphones could be built in as one unit. The first membrane 6 has a first pressure surface 6a open to said sample gas conduit 1, and the second membrane 7 has a second pressure surface 7a open to said reference gas conduit 2, whereupon said microphonic membranes are movable as responses to pressure changes in said sample gas conduit and in said reference gas conduit respectively. The pressure surfaces respect to those sides of the membranes against which gas pressures act. Especially according to the invention these two microphonic membranes 6 and 7 are parallel to each other, and further the pressure surfaces 6a and 7a of these parallel microphonic membranes are to the same direction T, or alternatively to the opposite directions T and −T. This means that microphonic membranes, which are normally planar but can also have other configuration, have their in mean or average planes parallel to each other in the state of rest thereof. The pressure surfaces 6a, 7a, which are in direct contact or possibly indirectly communicating with the gas pressure in the gas conduits 1, 2, are directed to the same direction T, or to the opposite directions T and −T. Typically the pressure detecting microphones 3, 4 have measuring cavities 10, 11 against said pressure surfaces of the microphonic membranes 6, 7, which cavities are connected to said sample gas conduit 1 and the reference gas conduit 2 through the passageways 8, 9 mentioned above. The passageways 8, 9 are preferably pipes or the like made of a flexible material. It shall be understood that the microphonic membranes 6, 7 can also have other configuration than planar, though this form is most universally used. For planar form the parallelism is self-evident, but if the membranes have a segmental form they are parallel when their chords are parallel. The independent microphonic membranes 6, 7 can be side by side, e.g. they or their chords may be in the same plane, or close to the same plane. It is, however, preferable that the microphonic membranes 6, 7 are at least approximately in line with a mutual distance in the direction of their central normals N1, N2, and at the same time the central normals N1, N2 have a spacing G, which is at maximum the sum of the transversal dimensions D1 and D2 of the membranes, or approach zero. In the first mentioned side-by-side case, together with a possible distance in direction of normals, the spacing may be larger than the sum of the transversal dimensions D1 and D2.

The pressure detecting microphones 3, 4 have electrical outputs $3_E$, $4_E$, which provide the signals S1, S2 that are proportional to the gas pressures in the sample gas and reference gas conduits 1, 2. The pressure detecting microphones 3, 4 preferably are condenser microphones, or electret microphones, or optical microphones, appropriate types of which are also commercially available, for example from Knowles Acoustics. Also other known or new type of microphones may be useful. The structure of the microphones are, accordingly, not necessary to describe in detail. That generally known feature may be mentioned that the movement of the membrane or membranes is arranged to give an electrical signal, which is to be proportional to the amount of membrane movement, which for its part is to be proportional to the pressure(s) against the membrane(s). The mentioned electronics 29 comprises an electrical/electronic subtraction unit 27 or addition unit 27, which have inputs $27_A$, $27_B$ that are connected to the electrical outputs $3_E$, $4_E$ of the pressure detecting microphones 3, 4. Depending of the electronic components there can be amplifiers 25, 26 between the electrical outputs $3_E$, $4_E$ of the microphones and the inputs $27_A$, $27_B$ of the subtraction/addition unit 27 to amplify the signals S1, S2. The subtraction/addition unit 27 produces a subtraction or addition signal at its output $27_S$ for forwarding the subtraction/addition signal to other components or devices, like further calculations and/or display. This subtraction/addition signal forms the analyzer output signal S3 and is the result of subtraction between or addition of signals S1 and S2 from the microphones. In practice the mentioned subtraction or addition is performed in a computer or in some other digital processing unit, whereupon the signals are at first gone through generally known analog-to-digital conversions, like A/D converters.

In operation an under-pressure is created into the analyzer output, which causes the sample gas and the reference gas to flow through the sample and reference gas conduits 1, 2 into the air gap 16 of the electromagnet, where the two gases mix up and exit through the opening 20 of the air gap 16, to the volume 18 and through outlet 19 out from the analyzer. When the oxygen content of the two gases in sample and reference gas conduits 1, 2 are equal, the magnetic gas pressure outside the magnetic air gap 16 in the sample gas conduit and the reference gas conduit as well as in the exit opening 20 must be equal. If the oxygen content of the two gases in sample and reference gas conduits are different and when the pulsed magnetic field is switched on by energizing the electric coil 17, a pressure difference will exist between the sample gas conduit 1 and the reference gas conduit 2 outside the air gap 16. This magnetic pressure difference, proportional to the oxygen content difference between the sample and reference gas conduits, is measured with the mentioned pressure detecting microphones 3 and 4.

In practice, although the oxygen contents of the two gases in sample and reference gas conduits are equal, a differential pressure signal exists between sample and reference gas conduit at the frequency of pulsed magnetic field. This pressure variation, let it be called magnetic ringing, is proportional to a magnetomechanical signal, which is due to an alternating mechanical force between the magnet poles and the magnetostriction of magnets core. If the pneumatic paths of the sample and reference gas conduits 1 and 2 are identical, the magnetic ringing has equal amplitude and phase in both sample and reference gas conduit. In practice there is some asymmetry in the pneumatic paths, which can be seen as amplitude and phase difference between the conduits 1 and 2, but also the properties of gases flowing in the sample and reference gas conduits may be different causing the associated pressure transfer function to be different.

Figure 2A:
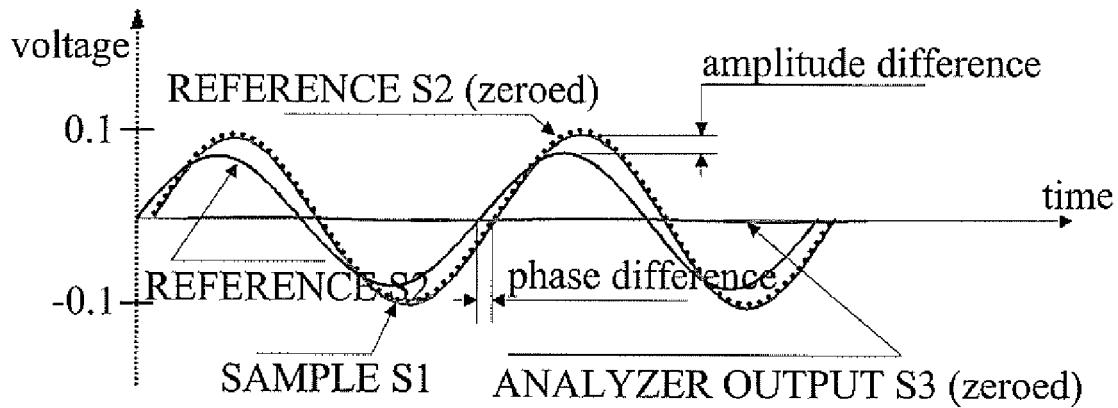
FIG. 2A shows the "raw" electrical pressure signals from the microphones and the analyzer output signal before calibration, when the sample gas and the reference gas has the same concentration of the paramagnetic gas component, and under static ambient conditions, i.e. without any mechanical shocks from outside.
Figure 2B:
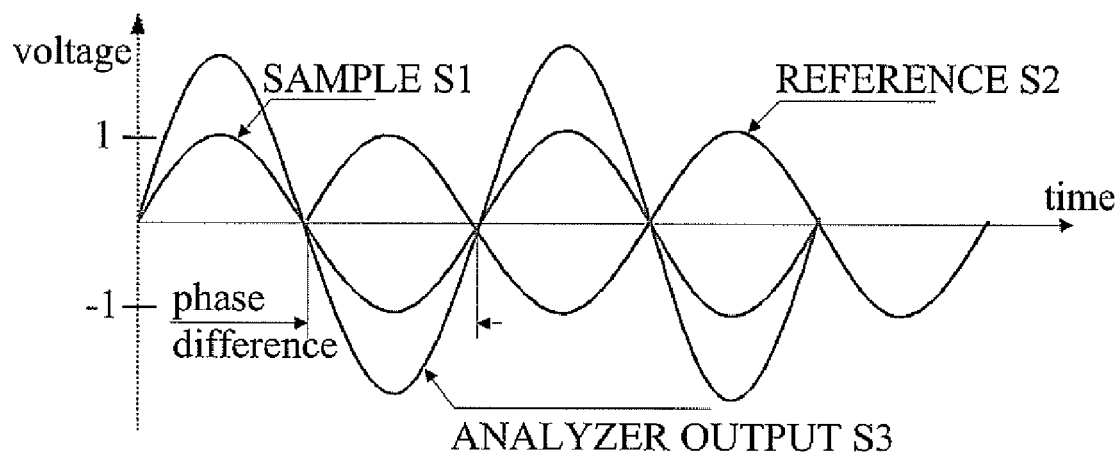
FIG. 2B shows the electrical pressure signals from the microphones and the analyzer output signal after calibration, when the sample gas is pure paramagnetic gas and the reference gas has a lower concentration of the same paramagnetic gas, and under static ambient conditions, i.e. without any mechanical shocks from outside.

Analyzer electrical output signal, which is proportional to the oxygen content in the sample gas, is a subtraction or addition of electrical output signals of pressure detecting microphones 3 and 4. Sample and reference signals S1 and S2 are used for calibrating the unmatched pressure sensing devices or asymmetrical pneumatic paths. When the oxygen content of the sample and the reference gases are equal, for example when measuring the room air, the magnetic ringing at the analyzer output can be zeroed by adjusting the amplification and the phase of signals S1 and/or S2 in amplifiers 25 and/or 26 so that the sample and the reference signals are equal for inputs $27_A$ and $27_B$ of the subtraction or addition unit 27. Any other electrical/electronic circuits suitable for this calibration can be used. FIG. 2A shows the sample and reference signals, as solid lines, before pressure signals have been calibrated, and the zeroed reference signal, as a dotted line, i.e. after the calibration. As mentioned, for calibration step the reference gas and the sample gas are arranged to have the same content of the paramagnetic gas component. The calibration, in this particular case, is done by adjusting the amplification and the phase of amplifier 26 by zeroing the "amplitude difference" and the "phase difference" so that the reference and the sample signals meet each other. The analyzer output signal S3, a continuous line, is a subtraction or addition of sample signal S1 and the zeroed reference signal S2, after the calibration. FIG. 2B shows this case after the calibration, when the sample gas is 100% $O_2$ and the reference gas is room air with 21% $O_2$ content. When the magnetic field is activated in the air gap 16 the magnetic pressure of oxygen in the sample gas conduit 1 becomes higher than the magnetic pressure of oxygen in the reference gas conduit 2 as they are compared to the magnetic pressure of oxygen in the exit opening 20. The alternating magnetic field causes the sample signal amplitude to vary proportional between the maximum and the minimum pressure in the sample gas conduit 1, whereas reference signal amplitude varies proportionally between the maximum and the minimum pressure in the reference gas conduit 2, but with the phase difference approaching 180° as the sample signal S1 has a phase lag compared to the reference signal S2. The amplitudes of sample and reference signals increase to multiples, usually 10 to 100 times higher, compared to the magnetic ringing signal at the same time. The amplitude of the analyzer output signal S3 is proportional to the sample and reference signals phase difference and the increase in amplitude. Presence of gases such as $N_2O$, He and $N_2$ cause small error to the analyzer output but is negligible at lower magnetic field frequencies such as 100 Hz to 500 Hz.

Figure 2C:
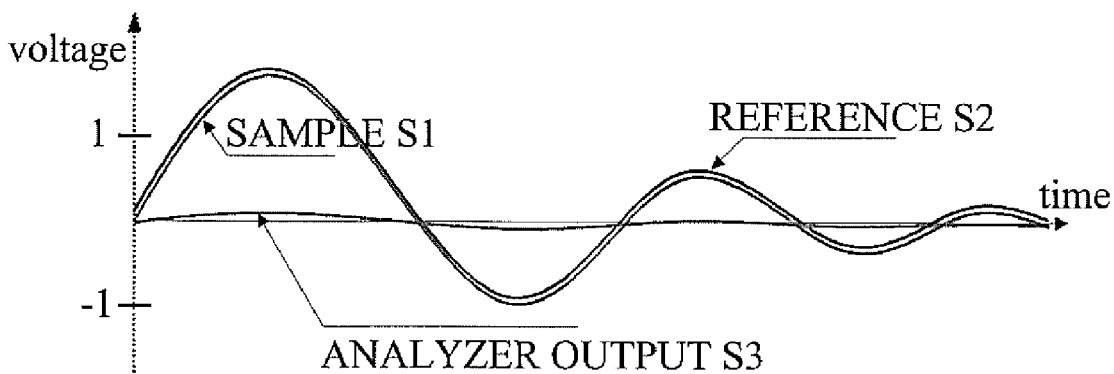
FIG. 2C shows the calibrated electrical pressure signals from the microphones and the analyzer output signal, when the sample gas and the reference gas has the same concentration of the paramagnetic gas component, and under dynamic ambient conditions, i.e. a mechanical shock is coming from outside.

The known oxygen analyzers based on magnetic pressure detection have been very sensitive to mechanical vibrations and acoustic background noise that interfere with the original oxygen signal. This is due to the construction of the available pressure sensing devices that are commonly based on detecting the surface pressure with a deflecting membrane or similar, which also corresponds to the construction of accelerometers. As the overpressure wave, caused by the oxygen molecules discharged from the magnetic trap in the air gap 16 as disclosed above, enter e.g. the microphone 3 through the passageway 8 into the measuring cavity 10 from the direction of sample gas conduit 1 in this particular case, the microphonic membrane 6 is deflected by the force pressing the first pressure surface 6a, as shown by the dotted line in FIG. 1. Opening 14 depressurizes the cavity 12 on the other side of the membrane 6 and hole 28 in membrane 6 is used for preventing the membrane to brake under static pressure, which is equalized over the membrane through the hole 28. When the oxygen molecules are trapped again into the magnetic field, an under pressure wave deflects the membrane similarly to the other direction—not shown—as was described previously. In the case of a mechanical shock MS1 directed from left to right as show in FIG. 1, the inertia of membrane's 6 mass causes the membrane 6 to lag in motion as the microphone moves rapidly to the right. The opposite phenomenon is present with opposite mechanical shock MS2. The motion of membrane 6 is similar to that caused by the above described overpressure wave, which can be seen as an electrical signal in the electric output, and causes erroneous signal in gas analyzers according to prior art. In the construction according to the invention these erroneous signals are avoided. Because there is two pressure detecting microphones 3 and 4 positioned symmetrically to each other so that the two microphonic membranes 6 and 7 are parallel to each other and their pressure surfaces 6a and 7a open to the same direction T, as shown in FIG. 1, a mechanical shock MS1 or MS2 in any direction is conducted to both microphonic membranes 6 and 7 in the same way. In this particular example shown in FIG. 1 the mechanical shock MS1 comes from the left, whereupon both membranes 6 and 7 deflect to the same direction as shown with a dashed line in FIG. 1, generating identical electrical output signals to same direction, if the pressure sensing devices differences are calibrated. In this special case the parallel pressure surfaces 6a and 7a open to the same direction T. It can be seen that when those identical interference signals are processed with the subtraction unit 27 the analyzer output S3 becomes insensitive for the mechanical shock or any vibration. If alternatively the parallel pressure surfaces 6a and 7a open to the opposite directions T and −T, a mechanical shock MS1 or MS2 in any direction is conducted to both microphonic membranes 6 and 7 in the same way like above, but the shock causes identical electrical output signals to opposite directions, whereupon the addition or summing is the valid operation between the sample signal S1 and the zeroed reference signal S2, instead of the subtraction valid when the pressure surfaces are to the same direction. It shall be understood that the mechanical shock can be of any kind and come from any direction, and however the two microphonic membranes 6 and 7 are always deflected the same amount to the same direction, whereupon the deflections cause the same deviation in the electrical pressure signals S1 and S2 either to same direction or to the opposite directions, which deviations are eliminated by the subtraction calculation—in case the pressure surfaces 6a and 7a are to same direction, or by the addition calculation respectively—in case the pressure surfaces 6a and 7a are to opposite directions in the subtraction/addition unit 27. FIG. 2C shown the effect of a mechanical shock on the electrical pressure signals S1 and S2 and the resulting analyzer output signal S3 in the paramagnetic gas analyzer of the invention. It is clear that amplifications shall be matched properly to attain the best possible elimination of error signals caused by mechanical affects. As can be seen the effect of the shock stays every moment eliminated from the analyzer output signal, and there is no need to wait until the mechanical attenuation diminishes the signals as would be necessary in the prior art gas analyzers. The system/arrangement of the invention in the gas analyzers eliminates not only the effects of mechanical shocks and vibrations, but even the effects of audible sounds coming from outside, which sounds the pressure detecting microphones would otherwise sense through the analyzer housing, i.e. all disturbances, which affect the microphonic membranes from outside can be eliminated either totally or at least lower to such a level that they can be neglected.

The effectiveness of the above mentioned inventive positioning of the microphones 3, 4 in the paramagnetic gas analyzer can be further enhanced by using a single internal stiff or solid support 40, in which the pressure detecting microphones 3 and 4 are rigidly fixed in such a position that the microphonic membranes 6, 7 are parallel to each other and the pressure surfaces 6a, 7a thereof are to the same direction T or to opposite directions T, −T. This way the pressure detecting microphones are fixed together through a common support that ensures accurately the same movement of both microphones under mechanical shocks. The two pressure detecting microphones 3 and 4 can be built as one unit, whereupon the body of the microphone combination forms this stiff or solid support 40. It is desirable that the mechanical vibration resonant frequency of the support 40 is lower—preferably much lower, e.g. lower than 20 Hz or 10 Hz—than the magnetic pressure measurement frequency, which is typically between 100 Hz and 500 Hz. It is also possible to use solid support 40, which has higher vibration resonant frequency than the magnetic pressure measurement frequency $f$ i.e. frequency of alternating electrical current or a chopped direct electrical current fed to the electromagnet 5 from the power source 60. The most important is that the solid support 40 does not have any mechanical resonant frequency at the magnetic pressure measurement frequency $f$, or preferably no mechanical resonant frequency near the magnetic pressure measurement frequency $f$. For this purpose the internal stiff support 40 is constructed to be a unitary piece of material, i.e. a single internal stiff support, and the material of the support is typically metal, but can also be reinforced plastic or molded plastic. The dimensions of the support are preferably selected to attain bending resistance at minimum 2 mm$^3$. Further, this internal stiff support 40 can be attached to the housing 70 using attenuatedly flexible one fixture or several fixtures 61, which have smaller rigidity than the support 40, whereupon the support 40 together with said microphones 3, 4 moves as one unit in respect to the housing 70 under possible motion shocks and/or air pressure shocks from the surrounding. The mentioned attenuated flexible fixtures 61 can be e.g. elastomer parts, or any other structure providing same kind of properties.

What is claimed is:

1. A paramagnetic gas analyzer with a housing, the paramagnetic gas analyzer comprising:
    an electromagnet that has spaced opposing magnetic poles forming an air gap with a magnetic field therebetween;
    a power source for supplying an electrical current to said electromagnet;
    a sample gas conduit and a reference gas conduit opening into said air gap, said sample gas conduit carrying a gas mixture to be analyzed, and said reference gas conduit carrying a reference gas having a known concentration of a gas;
    an exit conduit communicating with said air gap for removing the gas mixture and reference gases from said air gap with the magnetic field;
    two pressure detecting microphones positioned symmetrically to each other, one each connected, respectively, to said sample gas conduit and to said reference gas conduit for sensing gas pressures in the respective conduits, and giving respective electrical pressure signals; and
    electronics connected to said microphones, said electronics for receiving said electrical pressure signals to form an analyzer output signal,
    wherein each of said pressure detecting microphones comprise a microphonic membrane independent from the microphonic membrane of the other pressure detecting microphone, and that has a pressure surface open to one of said sample gas conduit and said reference gas conduit,
    wherein said pressure detecting microphones are fixed together in manner that causes similar movement of both microphones under a mechanical shock,
    wherein said microphonic membranes are movable as responses to pressure changes in said sample gas conduit and in said reference gas conduit respectively, and electrical outputs providing signals proportional to gas pressures in the sample gas and reference gas conduits, and
    wherein said microphonic membranes are parallel to each other so that said pressure surfaces oppose each other and are directed to the same direciton, or to the opposite directions in response to gas pressure in the gas conduits.

2. The paramagnetic gas analyzer of claim 1, wherein said pressure detecting microphones are condenser microphones, or electret microphones, or optical microphones.

3. The paramagnetic gas analyzer of claim 1, wherein each of said microphonic membranes has a transversal dimension and a central normal, and wherein the spacing between the normals being at maximum the sum of said transversal dimensions.

4. The paramagnetic gas analyzer of claim 1, wherein said pressure detecting microphones comprise measuring cavities against said pressure surfaces of the microphonic membranes, said cavities connected to said sample gas conduit and said reference gas conduit through passageways, and wherein said passageways are pipes made of a flexible material.

5. The paramagnetic gas analyzer of claim 1, wherein said electronics comprises an electrical/electronic subtraction or addition unit with inputs connected to said electrical outputs of the pressure detecting microphones through optional amplifiers, and with outputs that forward the subtraction/addition signal as the analyzer output signal.

6. The paramagnetic gas analyzer of claim 1, further comprising:
    a single internal stiff support, fixing said pressure detecting microphones.

7. The paramagnetic gas analyzer of claim 6, wherein said single internal stiff support is a unitary piece of material that comprises metal or reinforced plastic or molded plastic.

8. The paramagnetic gas analyzer of claim 6, characterized in that said single internal stiff support has a bending resistance of at least 2 mm$^3$.

9. The paramagnetic gas analyzer of claim 6, further comprising attenuatedly flexible fixture(s) attaching said single internal stiff support to said housing.

10. The paramagnetic gas analyzer of claim 9, wherein said single internal stiff support has greater rigidity than said attenuatedly flexible fixtures, and wherein said support moves together with said microphones as one unit in respect to the housing under the mechanical shock.

11. The paramagnetic gas analyzer of claim 9, wherein said attenuatedly flexible fixtures comprise elastomer parts.

* * * * *

UNITED STATES PATENT AND TRADEMARK OFFICE
CERTIFICATE OF CORRECTION

PATENT NO. : 7,726,176 B2  Page 1 of 1
APPLICATION NO. : 11/548885
DATED : June 1, 2010
INVENTOR(S) : Haveri It is certified that error appears in the above-identified patent and that said Letters Patent is hereby corrected as shown below:

In Column 3, Lines 10-11, delete "The invention is described below in detail with reference to the accompanying drawings, in which" and insert the same below Line 14, reading "BRIEF DESCRIPTION OF THE DRAWINGS".

In Column 10, Line 1, in Claim 1, delete "direciton" and insert -- direction, --, therefor.

In Column 10, Line 25, in Claim 6, delete "support," and insert -- support --, therefor.

Signed and Sealed this

Sixteenth Day of November, 2010

David J. Kappos
*Director of the United States Patent and Trademark Office*